US010252265B2

(12) United States Patent
Tatnell et al.

(10) Patent No.: US 10,252,265 B2
(45) Date of Patent: Apr. 9, 2019

(54) MICROFLUIDIC DEVICES AND ARRANGEMENTS FOR INTRODUCING REAGENTS AND BIOLOGICAL SAMPLES TO SUCH DEVICES

(71) Applicant: GE Healthcare UK Limited, Buckinghamshire (GB)

(72) Inventors: Peter James Tatnell, Cardiff (GB); Jeffrey Kenneth Horton, Cardiff (GB); Geraint Seymour, Cardiff (GB)

(73) Assignee: GE Healthcare UK Limited, Buckinghamshire (GB)

( * ) Notice: Subject to any disclaimer, the term of this patent is extended or adjusted under 35 U.S.C. 154(b) by 0 days.

(21) Appl. No.: 15/121,147

(22) PCT Filed: Feb. 20, 2015

(86) PCT No.: PCT/EP2015/053612
§ 371 (c)(1),
(2) Date: Aug. 24, 2016

(87) PCT Pub. No.: WO2015/132085
PCT Pub. Date: Sep. 11, 2015

(65) Prior Publication Data
US 2016/0367986 A1 Dec. 22, 2016

(30) Foreign Application Priority Data
Mar. 4, 2014 (GB) .................... 1403790.7

(51) Int. Cl.
*G01N 31/22* (2006.01)
*B01L 3/00* (2006.01)
*G01N 1/28* (2006.01)

(52) U.S. Cl.
CPC ........ *B01L 3/502715* (2013.01); *G01N 1/286* (2013.01); *B01L 2200/025* (2013.01);
(Continued)

(58) Field of Classification Search
USPC ...... 422/502–504, 512, 527, 568, 570, 68.1, 422/400–402, 408–410, 413, 417, 420,
(Continued)

(56) References Cited

U.S. PATENT DOCUMENTS 2,328,558 A * 9/1943 Kipp ..................... B26F 1/36
83/588
4,341,735 A 7/1982 Seifried
(Continued)

FOREIGN PATENT DOCUMENTS

WO 2010/127464 A1 11/2010
WO 2013/043562 A1 3/2013

OTHER PUBLICATIONS

International Search Report and Written Opinion regarding International Application No. PCT/EP2015/053612, dated May 8, 2015, 11 pages.
(Continued)

*Primary Examiner* — Dean Kwak
(74) *Attorney, Agent, or Firm* — Eversheds Sutherland (US) LLP (57) ABSTRACT

A microfluidic device 100 is disclosed comprising a body 112 including a biological sample S and/or reagent R receiving slot 122. The sample and reagent are carried on a solid support 10. The device 100 includes two punch assemblies 130 for removing portions of the solid support 10 and delivering them, together with the sample and/or reagent(s), to a receiving chamber 126 for subsequent processing. The device can be used for various assays including those which require just the addition of water in the reaction chamber with no pre-treatment of sample prior delivery into the chamber.

16 Claims, 2 Drawing Sheets

(52) U.S. Cl.
CPC ..... *B01L 2200/027* (2013.01); *B01L 2200/16* (2013.01); *B01L 2300/041* (2013.01); *B01L 2300/06* (2013.01); *B01L 2300/069* (2013.01); *B01L 2300/123* (2013.01); *G01N 2001/288* (2013.01)

(58) Field of Classification Search
USPC .................................................. 422/424, 425
See application file for complete search history.

(56) References Cited

U.S. PATENT DOCUMENTS

| | | | | |
|---|---|---|---|---|
| 4,477,575 A * | 10/1984 | Vogel | ................ | B01D 39/2017 210/509 |
| 4,764,987 A * | 8/1988 | Drei | ......................... | A41H 3/00 101/368 |
| 4,774,192 A * | 9/1988 | Terminiello | .......... | B01L 3/5023 422/417 |
| 5,135,716 A * | 8/1992 | Thakore | ................ | B01D 61/18 422/412 |
| 5,597,532 A * | 1/1997 | Connolly | ................ | B01L 3/545 422/401 |
| 6,171,849 B1 * | 1/2001 | Rittersdorf | ............... | C12Q 1/60 435/283.1 |
| 6,759,190 B2 * | 7/2004 | Lin | ......................... | C12Q 1/54 422/69 |
| 2004/0126830 A1 * | 7/2004 | Shull | .................... | G01N 33/526 435/11 |
| 2005/0003523 A1 * | 1/2005 | Anaokar | .................. | C12Q 1/44 435/287.2 |
| 2005/0129579 A1 | 6/2005 | Morrison | | |
| 2006/0062690 A1 * | 3/2006 | Lawrence | .............. | G01N 33/52 422/400 |
| 2006/0196768 A1 * | 9/2006 | Huang | ............... | G01N 27/3272 204/400 |
| 2012/0040470 A1 | 2/2012 | Dorn | | |
| 2012/0186368 A1 * | 7/2012 | Lehtonen | ................ | B01L 99/00 73/864.41 |
| 2016/0263577 A1 * | 9/2016 | Ismagilov | ........... | B01L 3/50273 |

OTHER PUBLICATIONS

GB Search Report regarding GB application No. 1403790.7, dated Jul. 1, 2014, 3 pages.

* cited by examiner

FIG. 1

MICROFLUIDIC DEVICES AND ARRANGEMENTS FOR INTRODUCING REAGENTS AND BIOLOGICAL SAMPLES TO SUCH DEVICES

CROSS-REFERENCE TO RELATED APPLICATIONS

This application is a filing under 35 U.S.C. 371 of international application number PCT/EP2015/053612, filed Feb. 20, 2015, which claims priority to GB application number 1403790.7, filed Mar. 4, 2014, the entire disclosures of each of which are hereby incorporated by reference.

This invention relates to microfluidic devices and arrangements for introducing reagents, and/or biological samples to such devices. In particular, but not exclusively, the invention is employable in molecular and biochemical assays, biological cell culturing, or other technologies which require microfluidics and reliable reagent supply, for example applications for miniaturised 'Lab on a chip' technologies which may be based around so called electrowetting or other microfluidic microchips, and stabilised reagent chemistries for supplying such technologies.

In this specification, 'reagent' means any material that is used to perform an assay or that facilitates an assay. The term reagent also encompasses constituent reagent materials that are combined, or reacted to form a reagent, and materials which stabilise samples.

Commercially available microfluidic devices typically have areas from 1 $mm^2$ to 10 $cm^2$ and are typically a few millimeters in thickness. Usually, such devices have a two-dimensional structure, but in some instances may be in three dimensions, including plural layers. The devices may be designed to contain a number of chambers which may be interconnected by either channels, tubes or zones apply electrostatic forces to transfer small amounts of fluid by a process known as electrowetting, wherein fluids are moved around. Different assay stages are performed at different locations on the device. Internal volumes of liquids required depend on the cross-section and geometry of the particular structures but are usually in the nanoliter to microliter range. The microfluidic devices may be fabricated from, for example, silicon, glass or different types of plastic e.g. polydimethyl siloxene (PDMS) or polymethylmethacrylate, or if designed without electrowetting, may involve the use of other known techniques including etching, hot embossing, wire imprinting, wax channel generation, reactive ion etching or laser ablation.

Other commercially available microfluidic devices include so called bioelectronic chips, which have an interface between biomolecules and non-biomolecule materials resulting in fluid transfer or movement of a droplet or modulation of the signal from the biomolecule to the device, wherein the sample can be moved electronically or amplified electrically. These bioelectronics chip devices contain built in electrical components or sit on electrical circuitry or PCB boards in combination with the fluidic elements. The electrical components (e.g. electrodes) are located within or below the device (e.g. within or below a micro chamber) and are used to manipulate a fluid or the components of fluid within the chamber or on the surface of the device.

The microfluidic devices mentioned above have the advantage that they can be employed by untrained staff, and in regions of the world where there are no laboratories. Usually a result can be obtained with little analytical skill.

However, the need to supply the devices mentioned above, and like devices, with reagents or biological samples has not been well considered to date. The use of untrained staff brings with it the risk of contamination of the reagents used, so an easy to use reagent and sample supply system is required. This problem has been addressed using sealed liquid reagent cassettes, for example as disclosed in US2007/0263049 published 15 Nov. 2007. Where multiple biological samples are collected, using a sealed supply container for each sample is not practical because samples are usually collected in the field, or at a clinic, and so sealing them correctly is difficult. Thus, a separate biological sample supply step is needed too. In addition, in hot climates the cooling of temperature sensitive reagents prior to their supply to a microfluidic device is problematic, particularly where no electricity is available.

Since it is possible to produce generic devices which can perform different tasks, simply by controlling the device in the correct manner, then it should be possible to produce relatively low cost multipurpose devices. However, then, each range of devices will need different reagents. If the reagents are required to perform an assay on a particular sample, then the sample too has to be introduced with the correct reagents to the device. So what should be a relatively low cost device can become more costly when the necessary customised supply hardware is included.

As an example, if a microfluidic device is to be used to detect different diseases based on the genetic signature of a blood sample, by means of a polymerase chain reaction (PCR) then different oligonucleotide primers will be required to perform the different detections. What is needed is a simple way to supply a number of different primers and as well as supplying a biological sample, that will be adequate for each detection. Conventionally, that would need a costly cassette based sealed liquid system which may need to be kept cool and would have a limited shelf life, plus the addition of a blood sample to be added to a cassette then sealed or otherwise preserved.

Current methods for DNA amplification in microfluidic devices involve a DNA purification procedure which often involves several steps which increases the chance of contamination. This is a complicated process and prior art methods have a number of clear disadvantages in terms of cost, complexity and in particular, user time. For example, column-based nucleic acid purification is a typical solid phase extraction method to purify nucleic acids. This method relies on the nucleic acid binding through adsorption to silica or other supports depending on the pH and the salt content of the buffer. Examples of suitable buffers include Tris-EDTA (TE) buffer or Phosphate buffer (used in DNA microarray experiments due to the reactive amines). The purification of nucleic acids on such spin columns includes a number of complex steps which require a complicated microfluidic device.

The inventors of the present invention have recognised the need for a very simple and low cost means for supplying reagents and samples to a microfluidic device, and have, in embodiments, addressed that need.

According to a first aspect, the invention provides a microfluidic device comprising a body including a receiving area for receiving a biological sample and/or one or more reagents, carried on a solid support, said device further including a means for removing a portion of the solid support and delivering said portion, together with the sample and/or reagent(s), to a receiving chamber at the receiving area.

The inventors have also realised that the processing of biological samples in microfluidic devices can be simplified.

According to a second aspect, the invention provides a method of using a microfluidic device to provide an assay, the method for including the following steps in any suitable order: a) providing a microfluidic device, having at least one receiving area for receiving a solid support carrying a biological sample, said device including a means for removing a portion of the support; b) removing a portion of the support which carries at least a portion of the sample; c) delivering the support portion carrying the sample to a receiving chamber; and d) operating the microfluidic device to process said portion according to the requirements of the assay.

The invention is further optionally characterised by the claims herein.

The invention extends to a microfluidic device or a method of operating the same, substantially as described herein optionally with reference to the drawings.

The invention can be put into effect in numerous ways. By way of example, embodiments are described below, with examples only being illustrated in the drawings, wherein.

Figure 1:
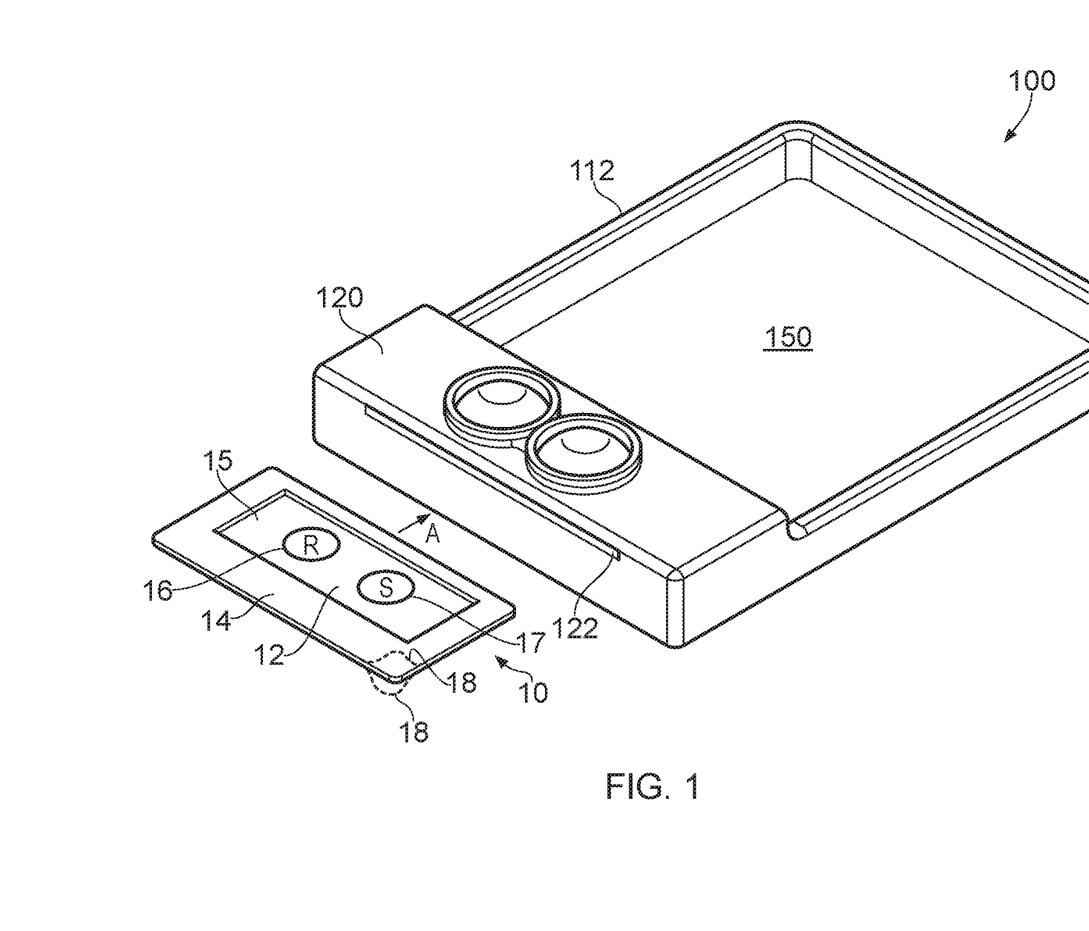
FIG. 1 shows a pictorial view of a microfluidic device and supply apparatus each according to the invention.

Referring to FIG. 1 there is shown a microfluidic device 100 including a body 112 having a receiving area 120 and fluid processing area 150. The receiving area 120 includes a slot 122, into which is inserted a reagent and biological sample holding mount apparatus 10.

The mount 10 includes a solid cellulose paper support 12, having a surrounding peripheral strengthening frame 14 formed from stiff card. The frame 14 has an opening 15 which exposes the support 12 and allows reagents R for biochemical assays, for example an enzyme to be deposited on the support at a reagent location 16 which, for example in the form of a slurry which is subsequently freeze dried. Other methods of applying a reagent are given below.

Whilst not essential, the apparatus includes a peel-off film 18, which is applied to both sides of the support 12 after the reagent is dried on the support.

In use, the film 18 is removed just before a sample S is applied to the mount 10 at a sample location 17. This sample is for example: a dried blood spot, blood plasma, urine, a cerebral culture media, cell cultures, tissue exudates and the like, containing an analyte, for example nucleic acid, a biopharmaceutical drug or drug metabolite.

The mount 10 with films 18 removed, and sample S applied, possibly after a long period of storage (possibly years), is fed in the direction of arrow A into the slot 122 of the microfluidic device 100. The device in this instance is capable of manipulating fluids by electrostatic charge as described above at a fluid processing area 150.

Figure 2:
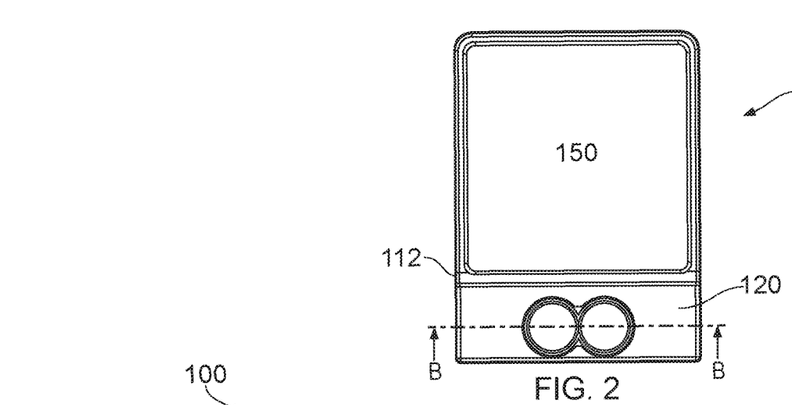
FIG. 2 shows a plan view of the device shown in FIG. 1.

Referring to FIG. 2, the device 100 is shown in plan view.

Figure 3:
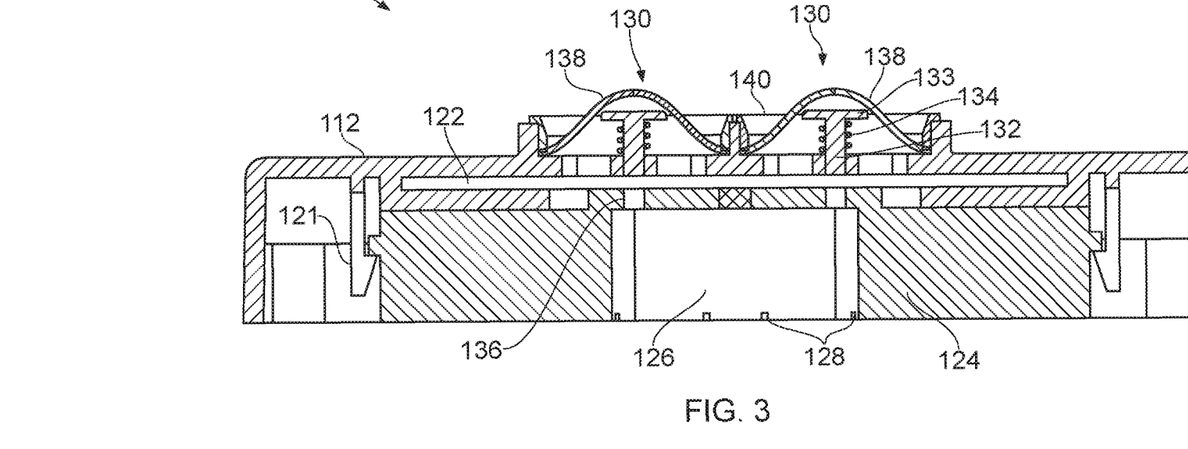
FIG. 3 shows a sectional view along the line B-B in FIG. 2.

Referring additionally to FIG. 3, there is shown a partial sectional view of the device 100 at the sectional line B-B in FIG. 2, without the mount 10 inserted therein. In this view the receiving area 120 of body 112 can be seen clipped to a manifold block 124 by means of spring clips 121 integrally moulded with the plastics body 112. The manifold block 124 includes a reaction chamber 126 which in turn is drained and filled via multiple ports 128 which lead to and from the fluid processing area 150.

The device 100 further includes two manually operable punch assemblies 13 which each have the same function, i.e. to cut a portion of the support 12 inserted into the slot 122, including either a sample S or a reagent R and force the cut portion into the reaction chamber 126 below.

Each punch assembly includes a punch 132 slideable in the body 112, having a head 133 and a return spring 134 which reacts with the head 133 and the body 112 to provide a restoring force to the punch 132. A punch die 136 is formed in the body 112 for each punch. Each assembly further includes an elastomeric cover 138 which seals the punch assemblies from external contamination. The covers are sealed around their edges by clamping piece 140 which clamps the seals to the body 112.

In practise, the apparatus 10 is inserted into the device 100 at slot 122 and by manually pushing down on each of the covers 138 a punched portion of the support 12 carrying a biological sample S and a punched portion carrying a reagent are forced into the reaction chamber for subsequent processing, for example thermal cycling, as described below.

One embodiment only is illustrated and described above, however it will be readily apparent that numerous modifications, additions, or omissions could be made, with departing from the scope of the invention defined herein. For example, apparatus 10 carrying both a biological sample and a reagent(s) is shown, but the apparatus 10 could carry only a biological sample or just reagent(s). Single or more than two punch assemblies could be used in place of the two shown.

Although reagents are intended to be stored in a substantially dry state on a support, further reagents, for example those which are common or generic to a plurality of assays may additionally be stored within the microfluidic device 100, for example at fluid processing area 150, for example sterile water.

EXAMPLES OF USE

Example 1. Direct Short Tandem Repeat Profiling

In this example, a blood sample from a suspected criminal is applied to the support 12 and allowed to dry. The apparatus 10 is inserted into the slot 122 and a portion of the support 12 is punched into the reaction chamber 126 in order to extract a sample of the DNA from the blood and is subjected to Short Tandem Repeat (STR) profiling. The resultant profile can then be cross matched to other samples on a criminal database facilitating the identification of the suspected criminal. In order to verify the procedure above, an experiment was carried out to amplify DNA directly from blood applied to a solid cellulose support matrix ('FTA Sample Collection Cards'; GE Healthcare, catalogue code: WB120205). The direct amplification procedure involves taking a 1.2 mm punch from a sample collection card on which a biological sample has been applied. This punch is added directly to the STR amplification mixture. This direct approach does not require a washing step to remove the chemicals associated with the FTA punch prior to downstream workflows.

Here, direct amplification of DNA from blood spots on FTA cards was undertaken. Direct STR profiling was carried out on duplicate samples using a PowerPlex 21 System (Product code DC8902, Promega, Southampton, UK) over 28 amplification cycles. The PowerPlex 21 System utilises four-colour fluorescent detection and facilitates the co-amplification of 21 loci (20 STR loci and Amelogenin), including D1S1656, D2S1338, D3S1358, D5S818, D6S1043, D7S820, D8S1179, D12S391, D13S317, D16S539, D18S51, D19S433, D21S11, Amelogenin, CSF1PO, FGA, Penta D, Penta E, TH01, TPOX and vWA. The PowerPlex 21 System provides all materials and reagents necessary to amplify the appropriate STR regions of human genomic DNA, including a hot-start thermostable DNA polymerase, master mix and primers. This kit was used to amplify DNA directly from 1.2 mm diameter samples punched from the FTA cards. The procedure was followed exactly as outlined in the instruction booklet (PowerPlex 21 System, Promega, Southampton, UK). Thermal cycling conditions over 28 cycles were as follows:

i. 96° C. for 1 minute;
ii. 94° C. for 10 seconds;
iii. 59° C. for 1 minute;
iv. 72° C. for 30 seconds for 28 cycles;
v. 60° C. for 20 minutes;
vi. 4° C. hold The resulting PCR products were separated using an ABI™ 3130xl Genetic Analyzer capillary electrophoresis system and analysed with GeneMapper™ ID v3.2 software (Life Technologies, Paisley, UK). The resultant STR profiles were interrogated and compared to standards and quality metrics such as peak heights etc.

This study demonstrated that full DNA STR profiles were obtained from the FTA paper which had been added directly to the STR reagent mix without undergoing a prior washing step. This indicates that a similar direct STR amplification approach using known microfluidic techniques can be readily applied and repeated using integrated microfluidic devices.

The example shows that DNA may be stored, recovered and amplified from this cellulose matrix, indicating that FTA may be used as a sample or reagent storage medium for the device outlined in this specification. The FTA punch is delivered to the microfluidics device as shown herein. In order to carry out the direct PCR reaction the STR assay reagents are delivered using the microfluidics device and PCR amplification and detection are carried out on board the device.

Example 2. Quantification of DNA from HeLa Cell Spotted and Blood Spotted FTA Elute Cards Using Direct Punch-in PCR Cultured HeLa cells at a concentration of $1 \times 10^7$ cell/ml or whole blood was spotted onto an indicating FTA elute card (iFTAe). A 3 mm or 1.2 mm punch was taken from the cell spotted FTA elute card and eluted using:

1. iFTAe high throughput elution protocol (98° C. on a heating block)
   Indicating FTA elute high throughput elution protocol was as follows:
   3 mm punch was punched into a reaction chamber, 200 µl of sterile water was added. The water was aspirated and discarded and 60 µl of sterile water was added and DNA eluted using the iFTAe high throughput elution protocol (98° C. for 30 mins on a heating block). Alternatively, the punch was:
2. washed with 1 ml of elution buffer or
3. left unwashed (direct assay, no wash).

Either the FTA card and associated sample or 5 µl of the eluate was added to the qPCR reaction containing TaqMan RNase P detection reagents and TaqMan Universal PCR master mix.

The PCR reaction was carried out as follows:
Standards and samples were added to the appropriate wells. The plates were sealed 50° C. for 2 min, followed by 95° C. for 10 min, followed by
40 cycles of: 95° C. for 15 sec, 60° C. for 1 min.
The detector used was the FAM™ probe. The results are presented in Table 1.

Ingredients—Volume
2× Universal Master mix—12.5 µl
Sterile water—11.25 µl
20× RNase P primer probe—1.25 µl
1.2 mm or 3 mm punch of FTA elute containing HeLa cells or 1.2 mm or 2×3 mm punch of FTA elute containing blood—1 punch All PCR reagents were delivered to the reaction chamber, of the type that could be used in a microfluidics device.

Table 1 shows the qPCR results of washed and unwashed blood spotted or cell spotted iFTAe card. The table shows the average yield of DNA from three qPCR reactions in ng/µl. The first 3 samples are replicates of DNA eluted (see method 1 above) from two 3 mm punches of iFTAe cards and the 4th sample is of a 1.2 mm punch of blood spotted iFTAe card that was washed with 1 ml of elution buffer and then amplified using real-time PCR (the data is the average of 3 separate samples) (method 2).

The washing steps were carried out in the reaction chamber with wash reagents subsequently delivered.

Samples 5 to 7 are replicates of DNA eluted from two 3 mm punch of an iFTAe card spotted with HeLa cells and the 8th sample is of a 3 mm punch HeLa spotted iFTAe card that was washed with 1 ml of elution buffer and then used in the real-time PCR machine (method 2).

The last sample was of a 1.2 mm punch of HeLa spotted iFTAe card that was not washed (method 3 above) and used directly in the real-time PCR machine (the data is the average of 3 separate samples). An unspotted negative punch did not yield any detectable DNA.

TABLE 1

Detection of DNA eluted from the punch following heating, punch washed with 1 ml elution buffer, or, punch analysed using direct (no wash) system.

| Sample | iFTAe punch size | Eluted/Direct Protocol | Average Yield (ng/µl) |
| --- | --- | --- | --- |
| Blood eluted from iFTAe Microcards (BATCH A) | 2 × 3 mm Punch | Eluted following iFTAe Protocol | 0.039 |
| Blood eluted from iFTAe Microcards (BATCH B) | 2 × 3 mm Punch | Eluted following iFTAe Protocol | 0.046 |
| Blood eluted from iFTAe Microcards (BATCH C) | 2 × 3 mm Punch | Eluted following iFTAe Protocol | 0.061 |
| Blood 1.2 mm from iFTAe Microcards | 1 × 1.2 mm Punch | Direct (washed 1 ml elution buffer) | 0.039 |

TABLE 1-continued

Detection of DNA eluted from the punch following heating, punch washed with 1 ml elution buffer, or, punch analysed using direct (no wash) system.

| Sample | iFTAe punch size | Eluted/Direct Protocol | Average Yield (ng/μl) |
| --- | --- | --- | --- |
| HeLa cells eluted from iFTAe Microcards (Batch A) | 1 × 3 mm Punch | Eluted following iFTAe Protocol | 6.025 |
| HeLa cells eluted from iFTAe Microcards (Batch B) | 1 × 3 mm Punch | Eluted following iFTAe Protocol | 5.099 |
| HeLa cells eluted from iFTAe Microcards (Batch C) | 1 × 3 mm Punch | Eluted following iFTAe Protocol | 5.956 |
| HeLa cells 3 mm from iFTAe Microcards | 1 × 3 mm Punch | Direct (washed 1 ml elution buffer) | 0.803 |
| HeLa cells 1.2 mm from iFTAe Microcards | 1 × 2 mm Punch | Direct (no wash) | 1.735 |

This study demonstrates that gDNA applied to and stored on a solid support such as cellulose-based sample collection cards in the form of either dried blood spots or tissue culture cells can be successfully extracted and quantified using direct punch in real-time PCR procedures in microfluidic devices.

The example shows that DNA may be stored, recovered and amplified from FTA Elute paper, indicating that this matrix may be used as a sample or reagent storage medium for the device outlined in this specification and PCR amplification assays carried out in a direct manner on board the device. Amplification and detection are carried out on board the device.

Example 3. Direct Amplification of Nucleic Acids in the Presence of Cyclodextrin and Using Prepared Freeze-Dried Reagent Mixtures The advantage of using freeze-dried or lyophilised reagents and formulations for a polymerase chain reaction is that these can be easily solubilized by the simple addition of water, thus saving operator time and facilitating reaction and sample throughput. To minimise operator error, the dried reagent mixture can be pre-dispensed into the reaction chamber 126 or an antechamber (not shown) in the microfluidics device.

The prepared freeze-dried reagent mixtures can be pre-formulated, pre-dispensed, stable at ambient temperature, and in the form of beads or cakes which allow amplification reactions to be carried out within a single chamber or reaction vessel and ensure greater reproducibility between reactions, minimize protocol steps, and, together with the device described and illustrated, reduce the potential for pipetting errors and contamination.

In this example there is provided a dried reagent, composition for nucleic acid amplification comprising, a sequestering reagent, a polymerase and a deoxyribonucleotide triphosphate (dNTP). The advantage of incorporating the sequestrant with the polymerase and dNTP into a dried reagent composition is to reduce the number of protocol steps required for nucleic acid amplification, thus reducing operator time and facilitating usage. In this example the nucleic acid is immobilised on a solid support in the form of a dried blood spot.

Here, the sequestering agent was a cyclodextrin. The cyclodextrin was selected from a group consisting of α-cyclodextrin, β-cyclodextrin, γ-cyclodextrin and derivatives thereof. Alternatively, the cyclodextrin could consist of a group consisting of 6-O-α-DMaltosyl-βcyclodextrin, hydroxyethyl-β-cyclodextrin, hydroxypropyl-β-cyclodextrin and 2-hydroxypropyl-β-cyclodextrin. The sequestrant was preferably α-cyclodextrin.

The solid matrix was selected from the group consisting of glass, glass fiber, glass microfiber, silica, silica gel, silica oxide, cellulose, nitrocellulose, carboxymethylcellulose, polyester, polyamide, carbohydrate polymers, polypropylene, polytetraflurorethylene, polyvinylidinefluoride, wool and porous ceramics. The solid matrix comprised of a glass or silica-based solid phase medium, a plastics-based solid phase medium or a cellulose-based solid phase medium. The solid support was a cellulose-based matrix.

Examples of cellulose-based matrices include FTA, 903 neonatal cards and 31-ETF cards available from GE Healthcare. The cellulose based matrix is in the form of a pre punched disc or in the form of an FTA pre punched disc. With FTA, the cell lysis reagent is embedded onto said solid matrix. In this case the lysis reagent comprises an anionic surfactant or detergent. Sodium dodecyl sulphate (SDS) is an example of an anionic surfactant frequently used to lyse biological cells. The amplification method comprises direct PCR, or direct reverse transcription (RT) polymerase chain reaction or isothermal amplification.

In this example, the polymerase is an OmniKlen Taq (OKT) Polymerase. Alternatively, the polymerase may be selected from the group consisting of T4 DNA Polymerase, Pol I and Klenow Fragment, T4 DNA Polymerase, Modified Bacteriophage T7 DNA Polymerase, Terminal Deoxynucleotide Transferase, Bst Polymerase, Taq Polymerase, Tth polymerase, Pow Polymerase, Vent Polymerase, Pab Pol I DNA Polymerase, Thermus thermophiles, Carboxydothermus hydrogenoformans, SP6 and SP7 RNA polymerase.

The preferred methodology is a dried reagent composition comprising α-cyclodextrin, at least one primer, a polymerase, dNTP, BSA, an excipient mix and an exchange buffer. The exchange buffer denote a buffer used for the removal of small ionic solutes, whereby one buffer is removed and replaced with another alternative buffer and for example may comprise of Tris/HCl, $CaCl_2$, a detergent, RE960 detergent, $MgCl_2$, KCl and nuclease free water.

A list of the chemicals and their sources is given below:
FTA papers for storing nucleic acid were obtained from GE Healthcare UK Limited;
Normal human blood (Tissue Solutions Ltd);
Genomic DNA (Promega product code G152A);
1 kb DNA ladder (Promega product code G571A);
Harris Uni-core punch, 1.2 mm (Sigma, Catalogue number Z708860-25ea, lot 3110);
OmniKlentaq Polymerase (Mo Bio Inc, catalogue code 1225-250);

Deoxyribonucleotide triphosphate (dNTP) (Life Technologies);
PCR Grade Bovine Serum Albumin (Life Technologies);
α-cyclodextrin (Fluka code 28705)
Sterile water (Sigma Product code W4502).
Excipient Mix:
Ficoll 70 (GE Healthcare);
Ficoll 400 (GE Healthcare) and
Melezitose (Sigma)
Cycle Sequence Mix 10×:
Trizma (Sigma);
KCl (Sigma);
MgCl (Sigma) and
Nuclease-free water (Sigma)
Exchange Buffer:
Tris/HCl pH 8.5 (Sigma);
1M $CaCl_2$ (Sigma);
1.0M $MgCl_2$ (Sigma);
2.0M KCl (Sigma) and
RHODAFAC RE-960 (7% RE960) (Kao Chemicals)

PCR reagents were combined with cyclodextrin and the excipient mix associated with RTG and the whole mixture lyophilised.

Punches containing samples were combined with water and the hydrolysed reagents from the lyophilised nucleic acid amplification composition or RTG cakes on a microfluidics plate and direct punch-in PCR was carried out (see below):

Direct PCR reactions were set up as follows:

Blood-spotted FTA was added to a receptacle with a nucleic acid amplification reagent cake that contained cyclodextrin or did not contain cyclodextrin (as a control). PCR was carried out on a Thermo Cycler following the manufacturer's user instructions.

The thermal cycling conditions were: 95° C. for 5 minutes, 95° C. for 30 sec, 55/65° C. for 1 min, 72° C. for 2 min followed by 35 cycles of: 95° C. for 30 sec, 55/65° C. for 1 min, 72° C. 2 min, followed by 72° C. for 10 mins.

The FTA punch is delivered to the microfluidics device as shown herein.

This example demonstrates that gDNA applied to and stored on cellulose-based sample collection cards in the form of a dried blood spot can be successfully amplified using reagents in a lyophilised storage format with solubilisation of the prepared freeze-dried reagent cakes or beads carried out on board the microfluidics device and PCR reagents delivered to the reaction chamber. Thermal cycling and detection are carried out on board the device.

Example 4. Reverse Transcription (RT) PCR of Total RNA

Reverse transcriptase (RT) is an enzyme used to generate complementary DNA (cDNA) from an RNA template, a process termed reverse transcription. Reverse transcriptase creates single-stranded DNA from an RNA template. Reverse transcription polymerase chain reaction (RT-PCR) is one of many variants of PCR. This technique is commonly used in molecular biology to detect RNA expression levels. RT-PCR is used to qualitatively detect gene expression through creation of complementary DNA (cDNA) transcripts from RNA. RT-PCR is used to qualitatively detect gene expression through creation of cDNA transcripts from RNA.

Human embryonic stem cells ($10^7$; GE Healthcare; cell line ref: WCB307 GEHC 28) were applied to solid support matrix e.g. FTA or 903 cards. Total RNA was extracted from the punches using a silica membrane under the following conditions. The sample containing punches were applied to a silica membrane in the presence of chaotropic ions and RNases in situ. The binding conditions were adjusted to favour adsorption of RNA to the silica membrane which would in practice be built into the microfluidics device. Contaminating DNA, which also bound to the silica membrane, was removed by the direct application of DNase I. Simple washing steps with two different buffers removed salts, metabolites and macromolecular cellular components. Finally, pure RNA was eluted under low ionic strength conditions with RNase-free water and RT PCR was carried out (see below):

Sample punching, extraction of RNA using (but not limited to) a silica membrane and delivery of RT PCR reagents can be carried on board the microfluidics device in practice. Punches containing samples were combined with water and the hydrolysed reagents from the lyophilised nucleic acid amplification composition or prepared freeze-dried reagent mixtures before amplification.

Yield of RNA was 312 ng/μl. Purity of RNA at 260/280 nm as measured on a spectrophotometer was 1.95.

RT PCR was carried out using a prepared freeze-dried reagent mixture sold under the brand name Illustra Ready to Go-RT PCR beads, 2.0 units of Taq polymerase, M-MuLV reverse transcriptase, 1.5 mM $MgCl_2$, 60 mM KCl, 10 mM Tris-HCL, stabilisers and 40 ng template RNA, prepared as above with RT-PCR carried out in 50 μl volumes following the general method outlined in example 3, with RTG lyophilised on board the microfluidics device.

Thermocycling conditions were as follows:
94° C., 3 min;
94° C. 30 secs;
55° C., 1 min;
72° C. 30 secs;
72° C. 5 mins;
42 cycles;
4° C. thereafter.

This example demonstrates that RNA can be extracted from cellulose-based sample collection cards and successfully amplified using RT-PCR reagents in a lyophilised storage format. The protocol and associated data described here shows that it is possible to extract and amplify RNA from the solid support matrix and to carry out analysis by RT-PCR on a microfluidics device using the appropriate techniques. Punches are delivered to the microfluidics device from collection cards and assay reagents delivered to a reaction receptacle on board. Thermal cycling and detection are carried out on the microfluidics device.

Example 5. Direct Enzyme Detection

Direct enzyme testing was carried out using reagents obtained from the DNase and RNase Contamination Kits (DNase & RNase Alert QC Systems, catalogue codes AM1970 & AM1966, Life Technologies). The reagents were used according to manufacturer's instructions.

In a first series of experiments, 0.125-0.5 units of DNase was applied to 903 paper in 10 μl volumes. In a second series of experiments, 1.2 mm punches were taken from $10^6$ human embryonic stem cells (GE Healthcare; cell line ref: WCB307 GEHC 28) which had been applied to, 903 cards in 10 μl volumes as above. In a third series of experiments, 1.2 mm punches were taken from $10^6$ human embryonic stem cells (GE Healthcare; cell line ref: WCB307 GEHC 28) containing either 0.5 unit of DNase or 10 µUnit of RNase added to these cells which had been applied to FTA and 903 papers in 10 µl volumes.

DNAse and RNase activity was measured as outlined below:

Assays were carried out "punch in well" with FTA punches directly suspended in DNase or RNase Alert Buffers.

Detection of DNase activity was carried out as follows using a cleavable fluorescent labelled DNase substrate. Lyophilized DNase Alert Substrate was dissolved in TE buffer (1 ml) and dispensed (10 µl). 10× DNase Alert Buffer (10 µl) and nuclease-free water (80 µl) was added and the test solution (100 µl) incubated for 60 minutes at 37° C. The DNase Alert QC System Substrate is a modified DNA oligonucleotide that emits a pink fluorescence when cleaved by DNase. For this assay, fluorescence was measured (excitation/emission 535/595 nm using medium gain). Solutions containing DNase activity produced a pink fluorescence, whereas solutions without DNase activity did not fluoresce. Thus, higher levels of DNase corresponded to an increase in the amount of light output. Negative controls consisted of nuclease-free water (80 µl) in place of sample.

Detection of RNase was carried out as follows using a cleavable fluorescent-labelled RNase substrate. Each punch was ejected into separate wells of 96-well plate. Lyophilized RNase Alert Substrate was dissolved in TE buffer (1 ml) and dispensed (10 µl). 10× RNase Alert Buffer (10 µl) and nuclease-free water (80 µl) was added and the test solution (100 µl) incubated for 60 minutes at 37° C. The RNase Alert QC System Substrate is a modified RNA oligonucleotide that emits a green fluorescence when cleaved by RNase. For this assay, fluorescence was measured (excitation/emission 485/535 nm using medium gain). Solutions containing RNase produced a green fluorescence, whereas solutions without RNase activity did not fluoresce. Thus, higher levels of RNase corresponded to an increase in the amount of light output. Negative controls consisted of nuclease-free water (80 µl) in place of sample.

These experiments demonstrated that DNase and RNase activity could be detected and quantified in a dose-dependent manner on sample collection cards in all three series of experiments. The protocols and associated data described here shows that it is possible to extract and detect 2 enzyme activities from a solid support matrix.

This demonstrates that similar steps can be successfully performed on microfluidics devices using the appropriate engineering techniques. Punches are delivered to the microfluidics device from collection cards and assay reagents delivered to a reaction receptacle on board the device. Heating and fluorescence detection are carried out on the microfluidics device.

Example 6. Direct Protein Detection

Recombinant IL-2±carrier (R & D Systems; Cat. 202-IL-CF-10 µg; lot AE4309112 and Cat. 202-IL-10 µg; lot AE4309081 respectively) was dissolved in blood (TCS Biosciences) at 50 pg or 100 pg/µl. Aliquots (1 µl containing 0, 50 or 100 pg of IL-2) were applied to GE Healthcare filter papers.

These samples were allowed to dry overnight at ambient temperature and humidity. 3 mm diameter punched disks were extracted from each paper type using the appropriately sized punch. Single discs were directly analysed for IL-2 with reagents from a fully configured IL-2 Quantikine ELISA kit (R & D Systems, Cat. D2050, lot 273275).

Direct assays were carried out "punch in well".

On completion of the assay the optical density was monitored at 450 nm. The recovery of IL-2 was determined by comparing values to a standard curve of known IL-2 concentrations.

As part of this proposal punches can be delivered to the microfluidics device from collection cards and assay reagents delivered to a reaction receptacle on board. Heating and optical density detection can be carried out on the microfluidics device.

Whilst six different assays have been described above, it will be apparent to the skilled addressee that the device described above has wide applicability, for example, it could be employed in the following assays:

1) Cell-based assays e.g: cell purification/sorting; cellular assays; stem cell differentiation; cardiac/hepatocyte differentiation; generation of cell clones; vector generation; transfection clonal selection; generation of labelled antibodies; single cell genomic amplification
2) Generic assays e.g: enzyme-linked immunosorbent assays, lateral flow assays, toxicological assays; single cell gel electrophoresis assays; enzymatic assays; cellular lysis; protein purification enzymatic assays;
3) Protein processes e.g: protein interactions; protein conjugation; protein-labelling; protein/peptide synthesis; sequential addition of amino acids; in-vitro troponin T protein expression; sequential protein purification; ion exchange; precipitation; antibody-based purification; recombinant protein purification; monitoring vaccine/protein production;
4) Nucleic acids processes e.g: nucleic acid synthesis; sequential addition of oligonucleotides; molecular biology manipulation (e.g enzyme digests, ligations); nucleic acid purification (e.g. DNA, tRNA, mRNA, cDNA, mtDNA); all-in-one nucleic acid labelling; generation of phage display libraries;
5) Human Identification and forensics e.g: DNA purification to STR/SNP analysis; FTA/FTA Elute and & indirect nucleic acid/protein operations; processing of sexual assault samples; forensic tissue typing by mRNA expression profiling; and/or
6) Diagnostics e.g: neonatal screening; immunocytochemistry; genotyping; identification of infectious diseases; genetic screening; assessments of disease predisposition;

There are a number of advantages in reducing the size/volume of known assay techniques to be compatible with the microfluidic device described above: (1) A reduction in the costs of biological materials consumed and the manufacturing processes resulting in cost-saving to the customer and to the business; (2) Integration of all the assay or sample processing steps (including sample preparation, handling or manipulation of analysis data, result preparation) which is essential in modern laboratory environments resulting in simplified operations; (3) Ease of use in field situations allowing for mobility; (4) Capability for multiple simultaneous testing (multiplexing) for many different analytes or analyses for example in multiple PCR approaches which can be done using TaqMan probes or spatial PCR, in proteomic studies or in multi-readout immunoassays; (5) Reduction in hazardous solid and liquid waste and packaging will result in a positive impact for the environment; (6) Elimination manual pipetting, reagent handling, reaction/process preparation and physical transfer of samples between equipment which consumes the majority of researchers' time; (7) The device and methods described here will change the way laboratory's work and will result in simplification of workflows and remove hands on requirements; (8) The technology described in this disclosure will offer flexible handling technology potentially eliminating pipetting and will provide alternatives to other common processes such as centrifugation, mixing purification & electrophoresis. Amplification of DNA directly from storage cards commonly used for preserving blood samples is particularly challenging due to assay or PCR inhibitors present in both blood, biological samples and on the storage cards themselves.

With conventional assays, a thorough washing protocol is required to remove the contaminants from the punch discs before PCR or other downstream analyses. The microfluidic system described in this patent allows amplification of DNA, detection of protein or enzyme directly from blood or other biological material stored on cards such as Whatman 903 ®, FTA® and FTA Elute® with no or very little pre-treatment or technical intervention. In summary the device can be used for various assays including those which require just the addition of water in the reaction chamber with no pre-treatment of sample prior delivery into the chamber. Use of cyclodextrin as a sequestering agent for SDS in the reaction chamber will aid the direct amplification of DNA and RNA, for example as described in Example 3. Total protocol times can be significantly reduced while maintaining good product yields with no nucleic acid or protein isolation and purification steps.

The invention claimed is:

1. A microfluidic device for assaying a biological sample, the device comprising:
   a single layer solid support impregnated with the one or more reagents including a weak base, a chelating agent, an anionic surfactant, and/or a chaotropic agent, and wherein the solid support carries both the one or more reagents and a biological sample, a body including a receiving area for receiving the biological sample and one or more reagents carried on the solid support, a receiving chamber at the receiving area, at least one microfluidic port, and a fluid processing area, wherein the receiving chamber is in microfluidic communication with the fluid processing area via said at least one microfluidic port such that the device is configured to assay the biological sample using microfluidics,
   at least one punch assembly for punching a portion of the solid support and delivering said portion together with the sample and the one or more reagents to the receiving chamber at the receiving area.

2. A microfluidic device as claimed in claim 1, wherein said punch assembly is manually operable.

3. A microfluidic device as claimed in claim 2, wherein the punch assembly includes a punch member, a die co-operable with the punch member, said punch member and die being relatively moveable to cut the portion from the support and to provide the delivery of the portion.

4. A microfluidic device as claimed in claim 3, wherein the device further includes at least one elastomeric cover member covering, the punch assembly and allowing said manual operation of the assembly.

5. A microfluidic device as claimed in claim 4, wherein at least one said elastomeric cover member is clamped to said body at the receiving area thereby providing a seal around the punch assembly.

6. A microfluidic device as claimed in claim 3, wherein the body at the receiving area includes a slot for accepting a solid support, wherein the punch member is mounted to the body at one side of the slot and is slidable in a path which extends through the slot, and wherein the die is formed by an aperture in the body on an opposing side of the slot in the path of the punch member.

7. A microfluidic device as claimed in claim 6, wherein the punch assembly further includes a return spring reacting between the body and a flattened head of the punch member.

8. A microfluidic device as claimed in claim 1 wherein the solid support is formed from material selected from the group consisting of a fibrous material, a cellulose fibre material, a glass fibre/microfibre material, a porous polymer, a porous membrane material, a polyester, a polyether sulfone (PES), a polyamide (Nylon), a polypropylene, a polytetrafluoroethylene (PTFE), a polycarbonate, a cellulose nitrate, a cellulose acetate, an aluminium oxide, a polysaccharide, an alginate, a cellulose, a modified cellulose and any combination thereof.

9. A microfluidic device as claimed in claim 8, wherein the support includes a biological sample comprising dried blood; blood plasma, or other blood components; urine; cerebral culture media; cell samples; cell culture; or tissue exudate.

10. A microfluidic device as claimed in claim 9, wherein the support holds at least one dry reagent at a first location, and a dry biological sample material(s) at a second location separate from the first location.

11. A method of using a microfluidic device to provide an assay, the method comprising the following steps:
   a) providing a microfluidic device comprising
      a single layer solid support impregnated with the one or more reagents including a weak base, a chelating agent, an anionic surfactant, and/or a chaotropic agent, and wherein the solid support carries both the one or more reagents and a biological sample,
      a body including a receiving area for receiving the biological sample and one or more reagents carried on the solid support, a receiving chamber at the receiving area, at least one microfluidic port, and a fluid processing area, wherein the receiving chamber is in microfluidic communication with the fluid processing area via said at least one microfluidic port such that the device is configured to assay the biological sample using microfluidics,
      at least one punch assembly for punching a portion of the solid support and delivering said portion together with the sample and the one or more reagents to the receiving chamber at the receiving area;
   b) removing the portion of the support which carries at least the portion of the sample;
   c) delivering the support portion carrying the sample to the receiving chamber; and
   d) operating the microfluidic device to process said portion according to requirements of the assay.

12. A method according to claim 11 further including the steps of:
   a) providing on the support the reagents in a dried or lyophilised state, for performing the assay;
   b) removing the portion of the support which carries at least the portion of the reagent(s); and
   c) delivering the removed portion carrying the reagent(s) to the reaction chamber; and wherein step d) includes hydrating the solid support in the chamber now containing the sample and the reagents, or introducing a solution into the chamber, in order to perform said assay.

13. A method according to claim 12, wherein the reagents include a sequestrant, such as cyclodextrin, for example α-cyclodextrin.

14. A method according to claim 11, wherein the punch assembly is manually operable, for example one or more manually operable punches to remove said portions and to deliver the portions to the chamber using the force transmitted by the punch during operation.

15. A method according to claim 13, wherein said assay includes amplification of nucleic acids carried on said portion, in the reaction chamber with no intervening steps between delivery and said amplification.

16. A method according to claim 13, wherein said assay includes detection or measurement of drugs, proteins or enzymes from the biological sample carried on said portion in the reaction chamber with no intervening steps between delivery and said detection or measurement.

\* \* \* \* \*